United States Patent
Li

(10) Patent No.: US 9,983,167 B2
(45) Date of Patent: May 29, 2018

(54) MULTICHANNEL POTENTIOSTAT ANALYZER SYSTEM AND METHODS

(71) Applicant: Zansors, LLC, McLean, VA (US)

(72) Inventor: Baichen Li, Falls Church, VA (US)

(73) Assignee: Zansors, LLC, Arlington, VA (US)

( * ) Notice: Subject to any disclaimer, the term of this patent is extended or adjusted under 35 U.S.C. 154(b) by 194 days.

(21) Appl. No.: 14/928,617

(22) Filed: Oct. 30, 2015

(65) Prior Publication Data

US 2016/0123921 A1    May 5, 2016

Related U.S. Application Data

(60) Provisional application No. 62/073,112, filed on Oct. 31, 2014.

(51) Int. Cl.
*G01N 27/416* (2006.01)

(52) U.S. Cl.
CPC .................. *G01N 27/416* (2013.01)

(58) Field of Classification Search
CPC ....... G01N 27/06; G01N 27/07; G01N 27/416
See application file for complete search history.

(56) References Cited

U.S. PATENT DOCUMENTS

| | | | |
|---|---|---|---|
| 4,599,146 A * | 7/1986 | Schattschneider | G01N 17/02 204/404 |
| 5,198,771 A * | 3/1993 | Fidler | G05F 1/561 204/230.1 |
| 7,774,038 B2 | 8/2010 | Wang et al. | |
| 8,133,369 B2 | 3/2012 | Tam | |
| 8,543,345 B1 | 9/2013 | Henry | |
| 8,604,810 B2 | 12/2013 | Sheppard, Jr. | |
| 2002/0014409 A1 * | 2/2002 | Matsumoto | C12Q 1/004 204/403.1 |

(Continued)

OTHER PUBLICATIONS

International Search Report directed to related International Application No. PCT/US/2015/058376, dated Jan. 20, 2016; 2 pages.

(Continued)

*Primary Examiner* — Thang Le
*Assistant Examiner* — Alvaro Fortich
(74) *Attorney, Agent, or Firm* — Sterne, Kessler, Goldstein & Fox PLLC

(57) ABSTRACT

The present disclosure outlines a device having a multi-channel potentiostat circuit and a microcontroller for controlling the multi-channel potentiostat circuit. The multi-channel potentiostat circuit includes a counter electrode, a reference electrode, and a first switch between the counter electrode and the reference electrode. The multi-channel potentiostat circuit also includes a plurality of measurement circuits coupled to respective second switches. The microcontroller can configured to provide a first signal to the multi-channel potentiostat circuit to control the first switch, wherein a state of the first switch changes an operating mode of the multi-channel potentiostat circuit. The microcontroller is also configured to provide a second signal to the multi-channel potentiostat circuit to control at least one of the second switches to couple at least one of the plurality of measurement circuits to a working electrode.

20 Claims, 5 Drawing Sheets

(56) References Cited

U.S. PATENT DOCUMENTS

| | | | |
|---|---|---|---|
| 2008/0223719 A1* | 9/2008 | Tam | G01N 27/3277 |
| | | | 204/403.01 |
| 2011/0025338 A1* | 2/2011 | Willey | G01N 27/42 |
| | | | 324/439 |
| 2012/0032366 A1* | 2/2012 | Ivniski | C22C 1/08 |
| | | | 264/51 |
| 2013/0217993 A1* | 8/2013 | Brunner | A61B 5/0536 |
| | | | 600/393 |

OTHER PUBLICATIONS

Written Opinion of the International Searching Authority directed to related International Application No. PCT/US/2015058376, dated Jan. 20, 2016; 2 pages.

\* cited by examiner

MULTICHANNEL POTENTIOSTAT ANALYZER SYSTEM AND METHODS

CROSS-REFERENCE TO RELATED APPLICATIONS

This application claims the benefit of U.S. Patent Application No. 62/073,112, filed on Oct. 31, 2014, which is incorporated herein by reference in its entirety.

BACKGROUND OF THE INVENTION

A conventional potentiostat uses an electrochemical cell with two or three electrodes, e.g., a reference electrode, a counter electrode, and a working electrode. The potentiostat is an electronic instrument that controls a voltage difference between a working electrode and a reference electrode. These electrodes are contained in an electrochemical cell. The potentiostat implements this control by injecting current into the cell through a counter electrode. In most applications, the potentiostat measures the current flow between the working electrode and the counter electrode.

The working electrode is the electrode where the potential is controlled and where the current is measured. Thus, the working electrode serves as a surface on which the electrochemical reaction takes place. The reference electrode is used to measure the working electrode potential and should have a constant electrochemical potential as long as no current flows through it. Lastly, the counter electrode is a conductor that completes the cell circuit and is generally an inert conductor. A current flowing into the solution via the working electrode leaves the solution via the counter electrode.

BRIEF DESCRIPTION OF THE DRAWINGS/FIGURES

DETAILED DESCRIPTION OF THE INVENTION

Figure 1:
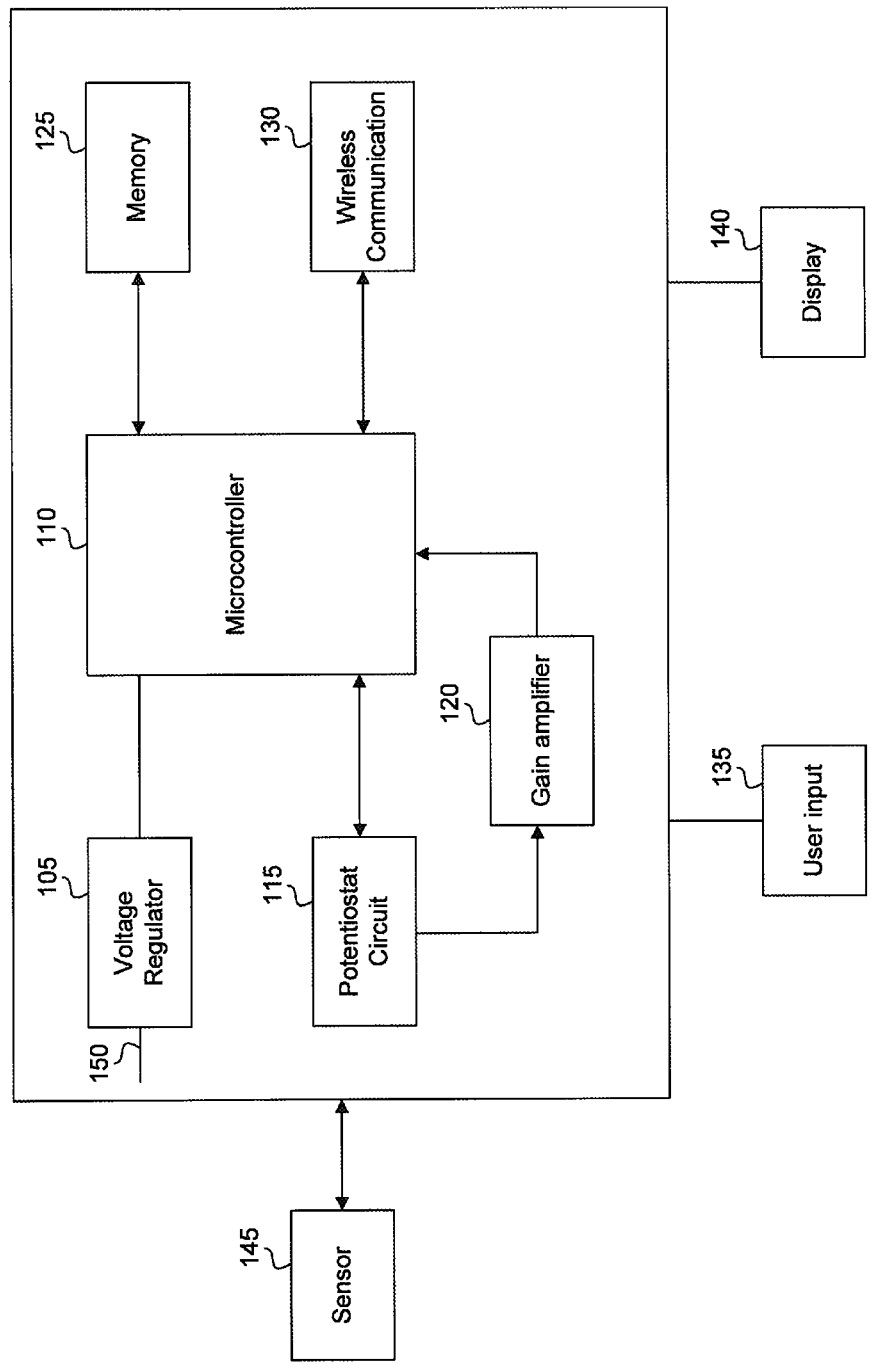
FIG. 1 illustrates a testing device in accordance with aspects of the present disclosure.

FIG. 1 illustrates a testing device in accordance with aspects of the present disclosure. As shown in FIG. 1, a testing device 100 includes a microcontroller 110, a voltage regulator 105, a multi-channel potentiostat circuit 115, a gain amplifier 120 (optional), a memory 125, and a wireless communications component 130.

The voltage regulator 105 receives a signal 150 from a power source and converts the signal 150 to a constant voltage level, e.g., 3.3V. For example, the testing device 100 may be powered using a connection to a computing device via a universal serial bus ("USB") connection. Alternatively, the power supply be an internal power supply, e.g., a lithium battery. In turn, the voltage regulator 105 provides a power signal 152 to the microcontroller 110. In other words, the voltage regulator 105 provides stabilized power, e.g., signal 152, to the microcontroller 110. Although the voltage regulator 105 can convert the signal 150 to a voltage level of 3.3V, a person of ordinary skill in the arts would understand that other constant voltage levels are contemplated by the present disclosure. In embodiments, the voltage regulator 105 may be a "feed-forward" or may include a negative feedback control loop. Alternatively, the voltage regulator may be a linear series regulator, a switching regulator, or a silicon controlled rectifier ("SCR") regulator.

The microcontroller 110 controls the operation of the multi-channel potentiostat circuit 115. For example, the microcontroller 110 provides a control signal to control an operating mode of the multi-channel potentiostat circuit 115. In embodiments, the control signal dictates whether the multi-channel potentiostat circuit 115 operates in a 2-lead operating mode or in a 3-lead operating mode. Furthermore, the microcontroller 110 provides a plurality of signals to the multi-channel potentiostat circuit 115 to couple a working electrode to a respective measurement circuit of the multi-channel potentiostat circuit 115 while decoupling remaining working electrodes from respective measurement circuits of the multi-channel potentiostat circuit 115. Alternatively, the plurality of control signals may couple a plurality of working electrodes to a respective measurement circuit when multiple measurement circuits share a same voltage bias or a same voltammetry functions. Thus, the microcontroller 110 selects one or more working electrodes to be used for testing a solution.

The multi-channel potentiostat circuit 115 measures analytes in a solution. For example, the multi-channel potentiostat circuit 115 can analyze a plurality of types of sensors for biomedical and environmental applications including water testing, blood testing, semen testing, DNA testing, urine testing, air quality testing and the like. Examples of analytes being tested can include multiple metabolites or metal ions. A person of ordinary skill in the art would recognize that these types of testing and analytes are exemplary only, and that other types of testing are also contemplated by the present disclosure.

The multi-channel potentiostat circuit 115 includes three electrodes, e.g., a counter electrode, a reference electrode, and a working electrode. In embodiments, the multi-channel potentiostat circuit 115 can be configured to operate using two electrodes, i.e., the counter electrode and the reference electrode. In this arrangement, the multi-channel potentiostat circuit 115

Alternatively, in embodiments, the multi-channel potentiostat circuit 115 is configured to operate using three electrodes. In such a configuration, electrochemical events at a given working electrode can be measured. To achieve this, the use of the three electrodes allows the potential and the current at the working electrode to be measured with little or no interference/contribution from the other electrodes. The multi-channel potentiostat circuit 115 measures and controls a voltage difference between a working electrode and a reference electrode. Additionally, the multi-channel potentiostat circuit 115 measures current flowing between the working electrode and a counter electrode.

The microcontroller 110 can receive measurements from the multi-channel potentiostat circuit 115. For example, using one or more measurement circuits, the multi-channel potentiostat circuit 115 can measure the analytes in a solution and provide the measurements to the microcontroller 110. In embodiments, the one or more measurement circuits amplifies the measurements before being transmitted to the microcontroller 110. Additionally, the one or more measurement circuits is coupled to a respective input of the microcontroller 110.

Alternatively, the microcontroller 110 can receive the measurements from the multi-channel potentiostat circuit 115 via the gain amplifier 120. For example, each measurement circuit of the multi-channel potentiostat circuit 115 is coupled to a respective input of the gain amplifier 120. The gain amplifier 120 amplifies the signal(s) from the multi-channel potentiostat circuit 115 and provides the amplified signal(s) to the microcontroller 110. In embodiments, the gain amplifier 120 amplifies a reaction current going through a working electrode to produce an output voltage of the multi-channel potentiostat circuit 115. In embodiments, the gain amplifier 120 can be a programmable gain amplifier such that the gain amplifier 120 can be programmed to amplified a designated signal(s). The gain amplifier 120 advantageously increases the dynamic range of the testing device 100. In embodiments, the gain amplifier 200 can amplify the output voltage of the multi-channel potentiostat circuit 115 by 200 fold.

The microcontroller 110 also communicates with the memory 125. The memory 125 can include a flash memory, RAM, ROM, or any other storage device that stores information to support the processing of the microcontroller 110, including measurements received from the multi-channel potentiostat circuit 115. Additionally, the memory 125 can store instructions utilized to control the multi-channel potentiostat circuit 115. For example, the memory 125 can also include computer-executable instructions, which when executed by the microcontroller 110, enable the microcontroller 110 to perform one or more functions described herein.

The microcontroller 110 also communicates with the wireless communications component 130. The wireless communications component 130 can be a Bluetooth component, near-field communication component, a wireless fidelity (Wi-Fi) component, long-term evolution component (LTE), or any other known wireless communication component. Using the wireless communication component 130, the testing device 100 can communicate with a remote computing device (not shown) or a cloud storage (not shown) via a wireless connection. The testing device 100 can communicate data measured using the multi-channel potentiostat circuit 115 to the remote computing device or the cloud storage. For example, the testing device 100 can be used by an Emergency Medical Technician ("EMT") to measure a patient's glucose level and the measured data can be transmitted to a receiving hospital. As another example, the testing device 100 can be used for on-site detection of Salmonella bacteria in water sample. In embodiments, the present disclosure provides an end-to-end solution because data from the multi-channel potentiostat circuit 115 can be geo-tagged and sent to a mobile cloud system providing a real-time display of the geo-mapping results. In embodiments, the geo-tagged data be used for current analysis/treatment as well as later spatial analyses, for example: (i) looking at pollution flows in real time; (ii) looking at geospatial patterns of biological, organic and inorganic pollutants; (iii) allowing early warning of public health hazards during emergencies, by monitoring upstream contaminants; or (iv) quick residential water testing after known contamination to determine safety.

The testing device 100 can be connected to a user input 135. In embodiments, a user can set parameters of a cyclic voltammetry function for the multi-channel potentiostat circuit 115 using the user input 135. The parameters can include scan range, scan rate, number of cycles, etc. The parameters can be stored in memory 125 and the microcontroller 110 can use these parameters to control the operation of the multi-channel potentiostat circuit 115. For example, the user hit a "start" button to run a test with specified parameters. The testing device 100 can also be connected to a display 140. In embodiments, once an experiment is finished, measurements can be plotted on the display 140 window for visual inspection. Thus, a user may input commands to control operations of the testing device 100 via the user input 135 and output results on the display 140. Additionally, in embodiments, the measurements can automatically be stored in a local hard disk of the remote computing device and the measurements can be further analyzed by other data analysis software.

The testing device 100 can also be connected to a biosensor 145. The biosensor 145 can include an electrode and a power source. In embodiments, the biosensor can be an aptamer-based sensor as described in U.S. Provisional Application No. 62/182,024, filed on Jun. 19, 2015, the contents of which are hereby incorporated by reference.

In embodiments, the biosensor 145 can also include the multi-channel potentiostat circuit 115. That is, according to aspects of the present disclosure, the multi-channel potentiostat circuit 115 may be integrated within the biosensor 145. The electrode may include 2-lead and 3-lead electrochemical sensors. The power source may be a battery or a wirelessly charging device. In embodiments, the biosensor 145 may include a dedicate device used to power the biosensor 145 and to receive data from the electrode. In embodiments, the biosensor 145 may further include a wireless communication component. For example, the wireless communication component may include an antennae, lasers, audio signals, RF, Bluetooth™, and/or various other methods to wirelessly transmit data. However, the present disclosure is not limited these components.

The biosensor 145 may further include an audio, visual, or tactile alert to notify users of specific events. For example, the alert(s) may be used to notify a user when an analyte exceeds (or falls) below a threshold level, and based on this information, the user can thereby perform procedures to address such, e.g., administer insulin when a glucose level is too. The multi-channel potentiostat circuit 115 integrated within the biosensor 145 may further include analog filters including an analog-to-digital converter ("ADC"). In embodiments, data obtained by the biosensor 145 may be processed using the microprocessor 110. Alternatively, the data recorded from the sensor 145 may be uploaded to the remote computing device and/or the cloud network for processing and/or storage.

Exemplary Microcontroller

Figure 2:
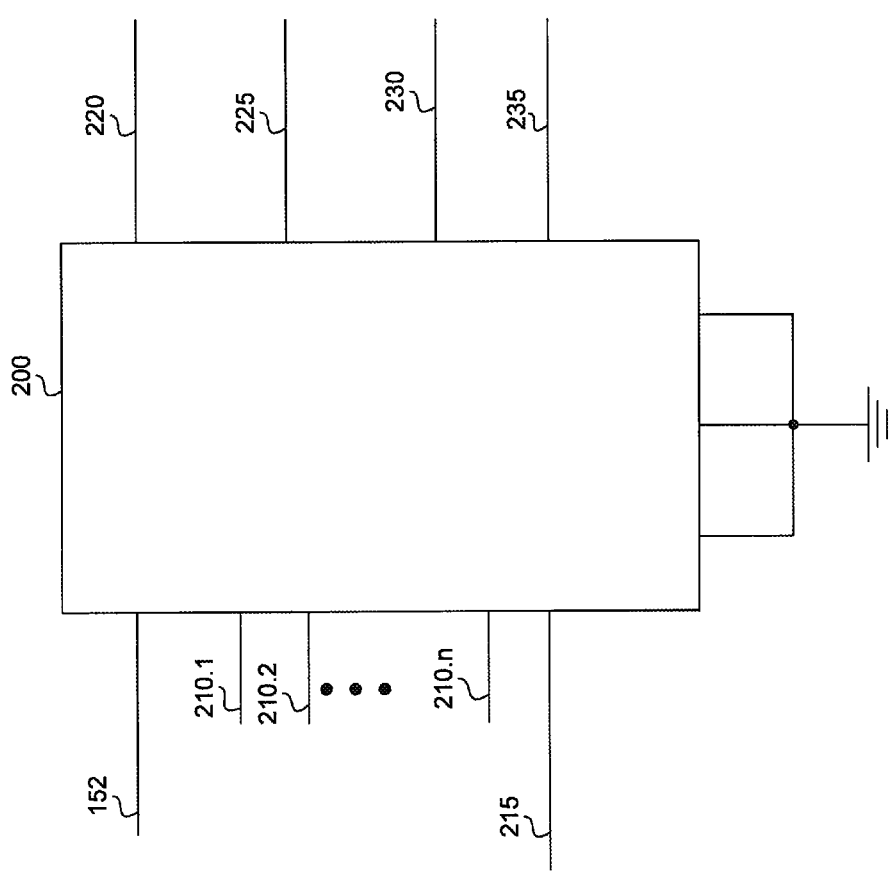
FIG. 2 illustrates an example microcontroller in accordance with aspects of the present disclosure.

FIG. 2 illustrates an example microcontroller in accordance with aspects of the present disclosure. A microcontroller 200 can be implemented as part of the testing device according to an exemplary embodiment of the present disclosure. The microcontroller 200 can communicate with a remote computing device computer, control voltammetry functions of a multi-channel potentiostat circuit, e.g., the multi-channel potentiostat circuit 115 of FIG. 1, and sample data from the multi-channel potentiostat circuit 115.

The microcontroller 200 provides a plurality of first signals 210.1 through 210.$n$ to a multi-channel potentiostat circuit. The plurality of first signals 210.1 through 210.$n$ are used to couple a working electrode to a respective measurement circuit of the multi-channel potentiostat circuit 115 while decoupling remaining working electrodes from respective measurement circuits. In this way, the microcontroller 200 selects a working electrode to be used for testing a solution. In embodiments, each of the plurality of first signals 210.1 through 210.$n$ of the microcontroller switches between a first logical value, such as a logical one to provide an example, and a second logical value, such as a logical zero. The microcontroller 200 selects a working electrode to a respective measurement circuit of the multi-channel potentiostat circuit 115 when a corresponding first signal, e.g., first signal 210.1, from among the plurality of first signals 210.1 through 210.$n$ is at the first logical value and de-couples the remaining working electrodes when the remaining first signals, e.g., first signals 210.2 through 210.$n$, are at the second logical value. Thus, in embodiments, the microcontroller 200 couples a single working electrode to a respective measurement circuit at a time. In embodiments, the microcontroller 200 can transmit multiple ones of the plurality of first signals 210.1 through 210.$n$ to couple multiple working electrodes to a respective measurement circuit such that multiple working electrodes are coupled to respective measurement circuits at a time.

The microcontroller 200 also provides a second signal 215 to the multi-channel potentiostat circuit 115 to control its operating mode. For example, the second signal 215 dictates whether the multi-channel potentiostat circuit 115 operates in a 2-lead operating mode or a 3-lead operating mode. In embodiments, the second signal 215 switches between a first logical value, such as a logical one to provide an example, and a second logical value, such as a logical zero. The second signal 215 dynamically controls a switch of the multi-channel potentiostat circuit 115. In embodiments, when the second signal 215 is a logical one, the switch is closed such that the multi-channel potentiostat circuit 115 operates in a 2-lead operating mode. Alternatively, when the control signal is a logical zero, the switch is open such that the multi-channel potentiostat circuit 115 operates in a 3-lead operating mode.

The microcontroller 200 also provides a third signal 220 to a memory, e.g., the memory 125 of FIG. 1. In embodiments, the third signal 220 can include a plurality of signals. For example, the third signal 220 can include a chip select signal, a master output/slave input signal, a master input/slave output signal, and/or a clock signal. Using these signals, the microcontroller 200 can store measurements received from the multi-channel potentiostat circuit 115 in the memory. Additionally, the memory 125 can use these signals to transmit instructions to the microcontroller 200 which are utilized to control the multi-channel potentiostat circuit 115.

In embodiments, the microcontroller 200 comprises a digital-to-analog converter ("DAC") which provides a fourth signal 225. The fourth signal 225 can be provided to the multi-channel potentiostat circuit 115 to control voltammetry functions, e.g., cyclic voltammetry functions, of the multi-channel potentiostat circuit 115. A POSA would understand that voltammetry is a category of electro-analytical methods used in analytical chemistry where information about an analyte is obtained by measuring the current as the potential is varied. Other exemplary voltammetry functions include linear sweep voltammetry, staircase voltammetry, square-wave voltammetry, anodic stripping voltammetry, cathodic stripping voltammetry, adsorptive stripping voltammetry, etc. In embodiments, the microcontroller can set the voltammetry based on the test being performed or the analyte being tested. Furthermore, the microcontroller 200 can also set the change the resolution of each channel of the multi-channel potentiostat circuit 115 based on the type of analyte being test.

The microcontroller 200 also provides a fifth signal 230 to a gain amplifier, e.g., the gain amplifier 120 of FIG. 1. In embodiments, the fifth signal 230 can include a plurality of signals. For example, the fifth signal 230 can include a chip select signal, a master output/slave input signal, a master input/slave output signal, and/or a clock signal. Using these signals, the microcontroller 200 can control operations of the gain amplifier. For example, the microcontroller 200 can be used to set the gain of the gain amplifier for each individual channel of the multi-channel potentiostat circuit 115. The microprocessor also receives a sixth signal 235 from the gain amplifier. The gain amplifier amplifies a measurement signal from the multi-channel potentiostat circuit and provides the amplified signal to the microcontroller 200. As discussed herein, the multi-channel potentiostat circuit 115 can be configured such that one working electrode is coupled to a respective measurement circuit of the multi-channel potentiostat circuit 115, while remaining working electrodes are de-coupled from the multi-channel potentiostat circuit 115. Thus, in embodiments, the sixth signal 235 represents an amplified signal from one of the measurement circuits of the multi-channel potentiostat circuit. These measurements can then be stored in the memory, transmitted to a remote computing device/cloud storage, or a combination of both. Alternatively, multiple working electrodes can be simultaneously coupled to their respective measurement circuits, and as such, the gain amplifier amplifies multiple measurement signals from the multi-channel potentiostat circuit. Thus, the sixth signal 235 can represent a combination of signals from the potentiostat circuit when multiple working electrodes are coupled to their respective measurement circuits.

Exemplary Multi-Channel Potentiostat Circuit

Figure 3:
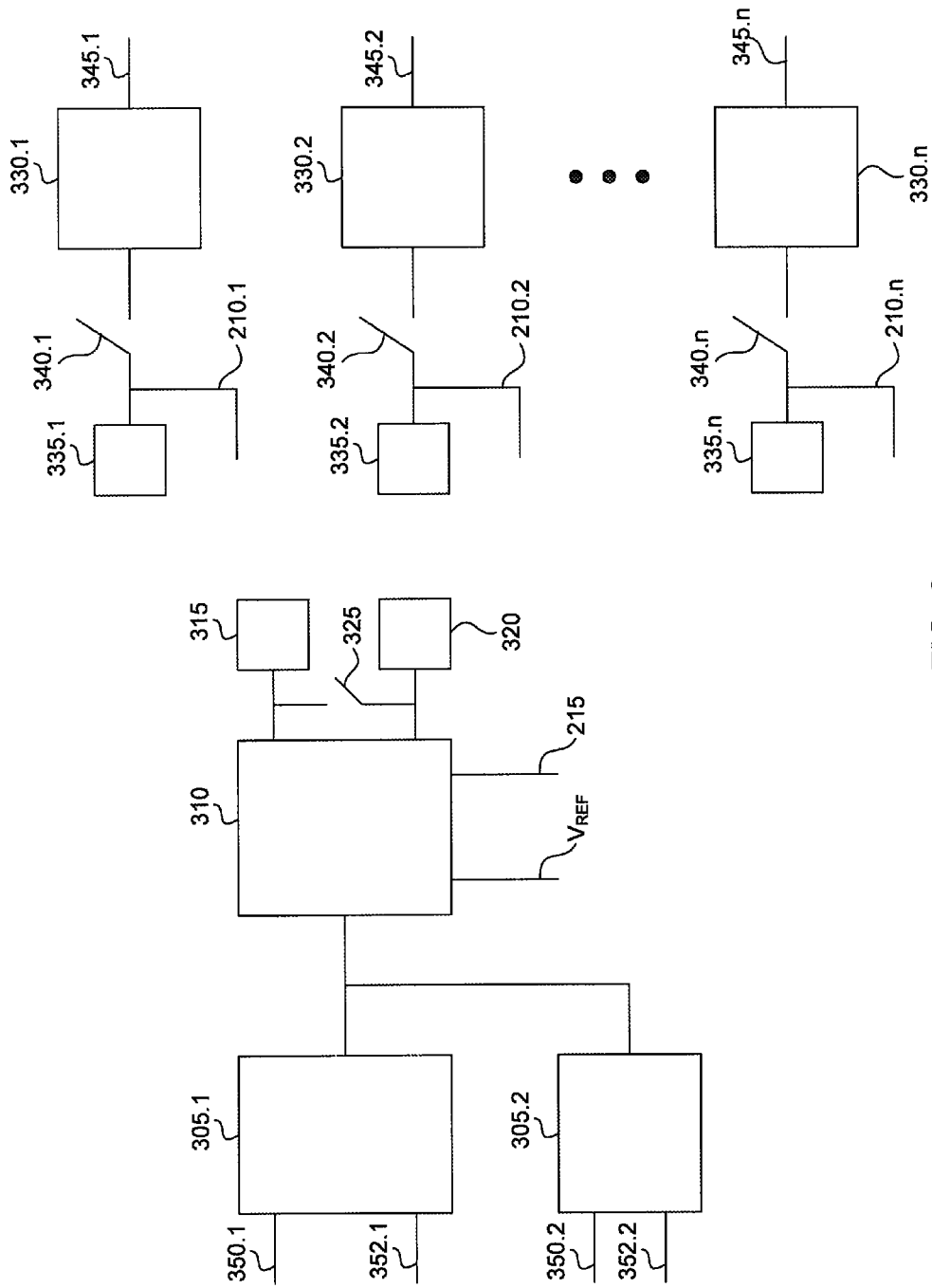
FIG. 3 illustrates an example multi-channel potentiostat circuit in accordance with aspects of the present disclosure.

FIG. 3 illustrates an example multi-channel potentiostat circuit in accordance with aspects of the present disclosure. A multi-channel potentiostat 300 can be implemented as part of the testing device according to an exemplary embodiment of the present disclosure. The multi-channel potentiostat circuit 300 comprises a first buffer 305.1, a second buffer 305.2, a feedback circuit 310, a counter electrode 315, a reference electrode 320, a switch 325, and a plurality of measurement circuits 330.1 through 330.$n$. In embodiments, the first buffer 305.1 and the second buffer 305.2 can each include an operational amplifier ("op-amp") and a resistor. In embodiments, the op-amp of the first buffer 305.1 and the second buffer 305.2 can be coupled to an external power supply, e.g., a boost voltage regulator, which can be used to expand the voltage range such that an output voltage at the counter electrode 315 may exceed a battery supply voltage. A first input 350.1 of the first buffer 305.1 can be coupled to a microcontroller, e.g., the microcontroller 200 of FIG. 2. For example, the first buffer 305.1 can be coupled to the fourth signal 225 from the microcontroller 200. A first input 350.2 of the second buffer 305.2 can be coupled to a waveform generator or a virtual ground. In embodiments, the waveform generator can be a sinusoidal waveform generator, a square waveform generator, a triangular waveform generator, etc.

A second input 352.1 of the first buffer 305.1 and a second input 352.2 of the second buffer can be coupled to respective input signals. The input signals represent signals of a voltammetry technique being applied to the multi-channel potentiostat circuit 300. In embodiments, a voltage applied at the reference electrode 320 serves as the reference voltage to a biosensor. Various voltammetry functions can be applied to the inputs based on the particular electrochemical techniques being utilized. For example, the voltammetry can be cyclical voltammetry, linear sweep voltammetry, staircase voltammetry, square-wave voltammetry, anodic stripping voltammetry, cathodic stripping voltammetry, adsorptive stripping voltammetry, etc.

An output of the first buffer 305.1 and an output of the second buffer 305.2 are combined as a single input provided to the feedback circuit 310. In embodiments, the feedback circuit can include an operational amplifier coupled to the counter electrode 315 and another operational amplifier coupled to the reference electrode 320. In embodiments, the op-amps of the feedback circuit 310 can also be coupled to an external power supply, e.g., a boost voltage regulator, which can be used to expand the voltage range such that an output voltage at the counter electrode 315 may exceed a battery supply voltage. In embodiments, a voltage Vref is applied to the feedback circuit 310. Additionally, a control signal, e.g., second signal 220 from microcontroller 200, is provided to the feedback circuit 310 to control the operation of the switch 325. The switch 325 can be analog switch, although other types of switches are also contemplated by the present disclosure. Additionally, the switch 325 can be implemented using a dual-switch configuration as would be understood by a POSA. In embodiments, the switch 325 is implemented between the counter electrode 315 and the reference electrode 320. As a result, the microcontroller 200 selects whether the multi-channel potentiostat circuit 300 operates in a 2-lead operating mode or a 3-lead operating mode. In embodiments, a default state of the switch 325 may be closed such that the counter electrode 315 and the reference electrode 320 are coupled to one another, which avoids a floating voltage.

In a conventional potentiostat circuit, two op-amps can be used to construct a feedback circuit, providing a fixed reference voltage the reference electrode and a sourcing/sinking current at the counter electrode. In the conventional potentiostat circuit, a connection is required between the counter electrode and reference electrode for the feedback circuit to function properly. However, when the system is powered up, the counter electrode and reference electrode are not connected, and consequently, the voltage at the counter electrode is an unknown value, i.e., a floating voltage. As a result, a large current may be forced through the working electrode, damaging the chemicals/coatings on the surface of the working electrode. This problem of conventional potentiostat circuits is resolved using the switch 325 between the counter electrode 315 and reference electrode 320 of the multi-channel potentiostat circuit 300. For example, when the multi-channel potentiostat circuit 300 is idle, a connection is formed between counter electrode 315 and reference electrode 320 thereby creating a closed loop system and stabilizing the voltage at both counter electrode 315 and reference electrode 320.

The plurality of measurement circuits 330.1 through 330.$n$ comprise a transimpedance amplifier, a resistor, and a capacitor. The plurality of measurement circuits 330.1 through 330.$n$ amplify a reaction current going through a respective working electrode from among the working electrodes 335.1 through 335.$n$. The plurality of measurement circuits 330.1 through 330.$n$ provide a respective output signal 345.1 through 345.$n$ to either a microcontroller or a gain amplifier. The output signals 345.1 through 345.$n$ represent a voltage output of the multi-channel potentiostat circuit 300.

The plurality of measurement circuits 330.1 through 330.$n$ are coupled to a respective working electrode 335.1 through 335.$n$ using a respective switch 340.1 through 340.$n$. In embodiments, the respective switches 340.1 through 340.$n$ are used to couple or de-couple the working electrodes 335.1 through 335.$n$ to the respective measurement circuits 330.1 through 330.$n$. In embodiments, the switches 340.1 through 340.$n$ are an analog switch such that no leakage current runs through the plurality of measurement circuits 330.1 through 330.$n$ when the switch is open. Although the switches 340.1 through 340.$n$ are described as being analog switches elements, a POSA would understand that any switch which prevents leakage current from pass through the measurement circuits 330.1 through 330.$n$ are contemplated by the present disclosure.

The switches 340.1 through 340.$n$ are open/closed based on a control signal provided by a microcontroller, e.g., first signals 210.1 through 210.$n$ from microcontroller 200. For example, each of the plurality of first signals 210.1 through 210.$n$ of the microcontroller switches between a first logical value, such as a logical one to provide an example, and a second logical value, such as a logical zero. In embodiments, when one of the first signals, e.g., first signal 210.1, is a logical one, and the remaining first signals, e.g., first 210.2 through 210.$n$, are a logical zero, the switch 340.1 is closed such the working electrode 335.1 is coupled to measurement circuit 330.1 while the remaining working electrodes 335.2 through 335.$n$ are de-coupled form their respective measurement circuits 330.2 through 330.$n$.

In this way, the microcontroller selects a working electrode to be coupled to a respective measurement circuit of the multi-channel potentiostat circuit 300. Each working electrode from among the working electrodes 335.1 through 335.$n$ may require different voltammetry functions, which results in various responses. As a result, to make the multi-channel potentiostat circuit 300 function properly and avoid interference, the switches 340.1 through 340.$n$ are utilized between each working electrodes 335.1 through 335.$n$ and its respective measurement circuit from among the plurality of measurement circuits 330.1 through 330.$n$. The switches 340.1 through 340.$n$ are also controlled by a microcontroller, e.g., microcontroller 200. In embodiments, the working electrodes 335.1 through 335.$n$ can be tested one-by-one, sequentially, with their own voltammetry functions. Thus, in embodiments, each measurement circuit may operate independently from each other such that the multi-channel potentiostat circuit 300 performs single-channel testing.

Alternatively, multiple ones of the plurality of first signals 210.1 through 210.$n$ can be used to close multiple switches 340.1 through 340.$n$ such that multiple working electrodes from among the working electrodes 335.1 through 335.$n$ are coupled to a respective measurement circuit from among the plurality of measurement circuits 330.1 through 330.$n$. As a result, the plurality of measurement circuits 330.1 through 330.$n$ can operate together when they share a same voltage bias or a same voltammetry functions.

The switches 340.1 through 340.$n$ are implemented between each working electrode 335.1 through 335.$n$ and a respective measurement circuit from among the plurality of measurement circuits 330.1 through 330.$n$. The switches 340.1 through 340.$n$ isolate an input pin of the measurement circuits 330.1 through 330.$n$ such that the measurement circuit 330.1 through 330.$n$ are turned on when the switch is closed and the measurement circuit 330.1 through 330.$n$ is turned off when the switching measurement is open. Consequently, when a switch is open, no current flows the respective measurement circuit thereby preventing any interference between the measurement circuits 330.1 through 330.$n$. Utilizing the plurality of measurement circuits 330.1 through 330.$n$ with a single counter electrode 315/reference electrode pair 320 reduces redundant circuitry. In contrast, conventional multi-channel potentiostat circuits utilize a counter electrode/reference electrode pair for each working electrode. Thus, conventional multi-channel circuits require redundant circuits that are large and expensive. In this way, the multi-channel potentiostat circuit of the present disclosure reduces both the overall size and costs of the testing device compared to conventional multi-channel potentiostat circuits.

Exemplary Gain Amplifier

Figure 4:
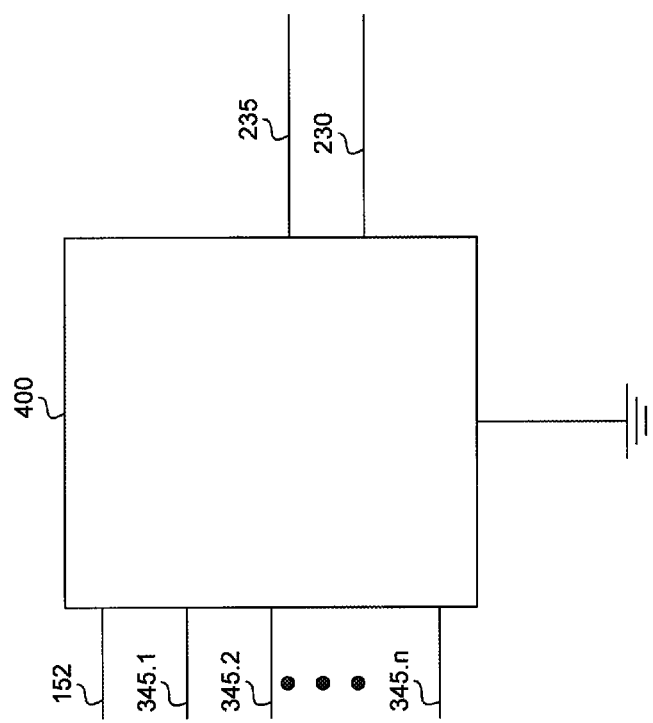
FIG. 4 illustrates an example gain amplifier in accordance with aspects of the present disclosure.

FIG. 4 illustrates an example gain amplifier in accordance with aspects of the present disclosure. A gain amplifier 400 can be implemented as part of the testing device according to an exemplary embodiment of the present disclosure. The gain amplifier 400 can be powered using the power signal, e.g., signal 152 as described with respect to FIG. 1. In embodiments, the gain amplifier 400 receives an input signal from a microcontroller, e.g., the fifth signal 230 from the microcontroller 200 of FIG. 2. As discussed herein, the fifth signal 230 can include a plurality of signals, e.g., a control signal, a master output/slave input signal, a master input/slave output signal, and/or a clock signal.

The gain amplifier 400 also receives a plurality of signal from a potentiostat circuit, e.g., output signals 345.1 through 345.n from the potentiostat circuit 300 of FIG. 3. The output signals 345.1 through 345.n represent a voltage output of the multi-channel potentiostat circuit 300. In embodiments, the gain amplifier 400 can be a programmable gain amplifier configured to amplify one or more of the output signals 345.1 through 345.n based on the signal 230 received from the microcontroller 200. The gain amplifier 400 advantageously increases the dynamic range.

The gain amplifier 400 also provides the amplified output signals to the microprocessor. The gain amplifier amplifies one or more of the output signals 345.1 through 345.n from the multi-channel potentiostat circuit 300 and provides the amplified signal to the microcontroller 200. For example, the gain amplifier provides an output signal, e.g., the sixth signal 235, to the microcontroller 200. The gain amplifier 400 can amplify one or more of the output signals 345.1 through 345.n by 200 fold. As discussed herein, the multi-channel potentiostat circuit 300 can be configured such that one working electrode is coupled to a respective measurement circuit of the multi-channel potentiostat circuit 300, while remaining working electrodes are de-coupled from the multi-channel potentiostat circuit 300. Thus, in embodiments, the output signal of the gain amplifier 400 represents a single amplified signal from one of the measurement circuits of the multi-channel potentiostat circuit. Alternatively, multiple working electrodes can be simultaneously coupled to their respective measurement circuits, and as such, the gain amplifier 400 amplifies multiple measurement signals from the multi-channel potentiostat circuit 300. Thus, the output signal of the gain amplifier 400 can represent a combination of signals from the multi-channel potentiostat circuit 300 when multiple working electrodes are coupled to their respective measurement circuits.

Exemplary Process of Operating a Multi-Channel Potentiostat Circuit

Figure 5:
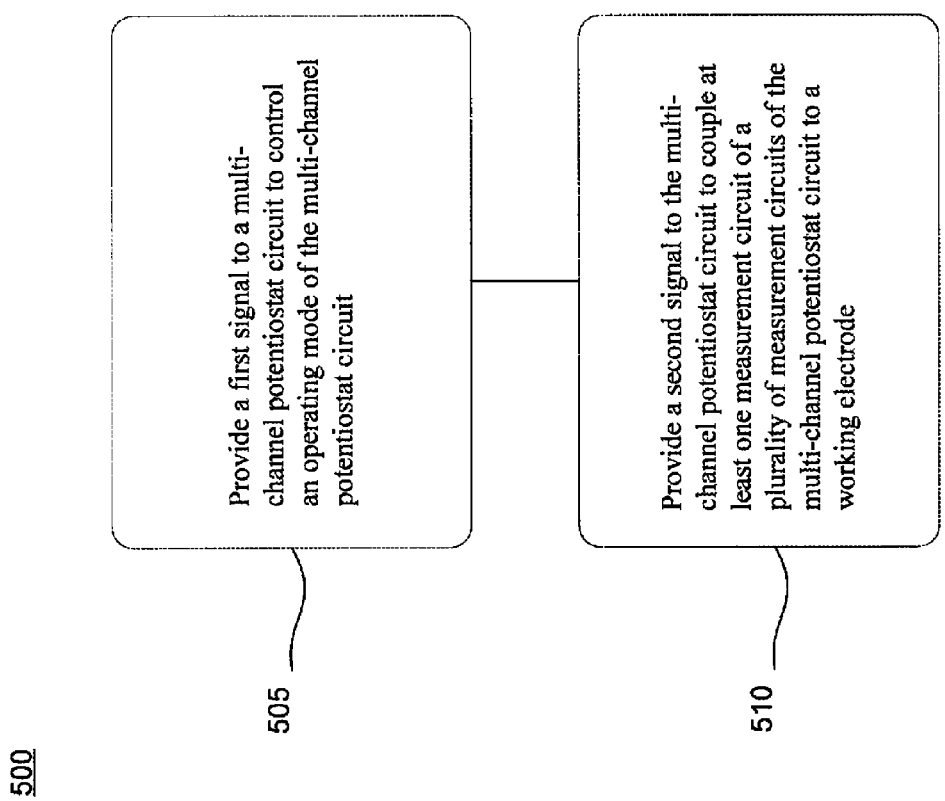
FIG. 5 illustrates an example process of operating a multi-channel potentiostat circuit in accordance with aspects of the present disclosure.

FIG. 5 illustrates an example process of operating a multi-channel potentiostat circuit in accordance with aspects of the present disclosure. A process 500 includes providing a first signal to a multi-channel potentiostat circuit to control an operating mode of the multi-channel potentiostat circuit at step 505. In embodiments, the operating mode comprises a 2-lead operating mode and a 3-lead operating mode. The multi-channel potentiostat circuit operates in the 2-lead operating mode when the first signal causes a switch to close and operates in the 3-lead operating mode when the first signal causes the switch to open. The process further includes providing a second signal to the multi-channel potentiostat circuit to couple at least one measurement circuit of a plurality of measurement circuits of the multi-channel potentiostat circuit to a working electrode at step 510. In embodiments, when the multi-channel potentiostat operates in the 3-lead operating mode, the second signal comprises a plurality of control signals, and the plurality of measurement circuits are sequentially coupled to respective working electrodes via second switches based on the plurality of control signals. Alternatively, when the multi-channel potentiostat operates in the 3-lead operating mode, the second signal comprises a plurality of control signals, and multiples ones of the plurality of measurement circuits can be simultaneously coupled to respective working electrodes via second switches based on the plurality of control signals.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

What is claimed is:

1. A device comprising:
   a multi-channel potentiostat circuit comprising:
      a counter electrode and a reference electrode, a stabilizing switch configured to switch between electrically coupling the counter electrode to the reference electrode and electrically isolating the counter electrode from the reference electrode,
a first interference switch of a plurality of interference switches configured to switch between electrically coupling a first measurement circuit of a plurality of measurement circuits to a corresponding first working electrode of a plurality of working electrodes, and electrically isolating the first measurement circuit from the corresponding first working electrode, and
a second interference switch of the plurality of interference switches configured to switch between electrically coupling a second measurement circuit of the plurality of measurement circuits to a corresponding second working electrode of the plurality of working electrodes, and electrically isolating the second measurement circuit from the corresponding second working electrode; and
a microcontroller configured to:
provide a first signal to the multi-channel potentiostat circuit to control the stabilizing switch, wherein a state of the stabilizing switch changes an operating mode of the multi-channel potentiostat circuit, and
provide a second signal to the multi-channel potentiostat circuit to control at least one of the plurality of interference switches to couple at least one of the plurality of measurement circuits to its corresponding working electrode of the plurality of working electrodes,
wherein measurements on each of the plurality of working electrodes are produced with respect to the counter electrode and/or the reference electrode.

2. The device of claim 1, wherein the first signal indicates whether the multi-channel potentiostat circuit operates in a 2-lead operating mode or in a 3-lead operating mode.

3. The device of claim 2, wherein the multi-channel potentiostat circuit operates in the 2-lead operating mode when the stabilizing switch is closed and the multi-channel potentiostat circuit operates in the 3-lead operating mode when the stabilizing switch is open.

4. The device of claim 1, further comprising a gain amplifier configured to amplify one or more outputs of the multi-channel potentiostat circuit and to provide an amplified output to the microcontroller.

5. The device of claim 1, wherein a default state of the stabilizing switch is closed to prevent a floating voltage.

6. The device of claim 1, wherein the microcontroller is configured to sequentially close each of the plurality of interference switches to couple each of the plurality of measurement circuits to its corresponding working electrode of the plurality of working electrodes one-by-one.

7. The device of claim 1, wherein the second signal comprises two or more control signals configured to simultaneously close corresponding two or more of the plurality of interference signals switches to couple respective working electrodes of the plurality of working electrodes to their corresponding measurement circuits of the plurality of measurement circuits when the corresponding measurement circuits of the plurality of measurement circuits share a same voltage bias or a same voltammetry function.

8. The device of claim 1, wherein the device is powered using a connection to a computing device via a universal serial bus ("USB") connection.

9. A multi-channel potentiostat circuit comprising:
a counter electrode and a reference electrode;
a stabilizing switch configured to switch between electrically coupling the counter electrode to the reference electrode and electrically isolating the counter electrode from the reference electrode;
a first interference switch of a plurality of interference switches configured to switch between electrically coupling a first measurement circuit of a plurality of measurement circuits to a corresponding first working electrode of a plurality of working electrodes, and electrically isolating the first measurement circuit from the corresponding first working electrode; and
a second interference switch of the plurality of interference switches configured to switch between electrically coupling a second measurement circuit of the plurality of measurement circuits to a corresponding second working electrode of the plurality of working electrodes, and electrically isolating the second measurement circuit from the corresponding second working electrode,
wherein measurements on each of the plurality of working electrodes are produced with respect to the counter electrode and/or the reference electrode.

10. The multi-channel potentiostat circuit of claim 9, wherein the multi-channel potentiostat circuit is configured to operate in a first operating mode or a second operating mode based on a control signal.

11. The multi-channel potentiostat circuit of claim 10, wherein the first operating mode is a 2-lead operating mode and the second operating mode is a 3-lead operating mode.

12. The multi-channel potentiostat circuit of claim 11, wherein the multi-channel potentiostat circuit operates in the 2-lead operating mode when the stabilizing switch is closed and the multi-channel potentiostat circuit operates in the 3-lead operating mode when the stabilizing switch is open.

13. The multi-channel potentiostat circuit of claim 9, wherein each of the plurality of interference switches are configured to be sequentially closed to couple each of the plurality of measurement circuits to its corresponding working electrode of the plurality of working electrodes one-by-one.

14. The multi-channel potentiostat circuit of claim 9, wherein two or more of the plurality of interference switches are configured to be closed simultaneously to couple respective working electrodes of the plurality of working electrodes to their corresponding measurement circuits of the plurality of measurement circuits when the corresponding measurement circuits of the plurality of measurement circuits share a same voltage bias or a same voltammetry function.

15. The multi-channel potentiostat circuit of claim 9, wherein a default state of the stabilizing switch is closed to prevent a floating voltage.

16. A method for operating a multi-channel potentiostat circuit comprising:
providing a first signal to the multi-channel potentiostat circuit to control an operating mode of the multi-channel potentiostat circuit by switching a stabilizing switch between electrically coupling a counter electrode to a reference electrode and electrically isolating the counter electrode from the reference electrode; and
providing a second signal to the multi-channel potentiostat circuit to control at least a first interference switch of a plurality of interference switches, the first interference switch configured to switch between electrically coupling a first measurement circuit of a plurality of measurement circuits of the multi-channel potentiostat circuit to a corresponding first working electrode of a plurality of working electrodes, and electrically isolating the first measurement circuit from the corresponding first working electrode, wherein the plurality of interference switches comprise a second interference switch configured to switch between electrically coupling a second measurement circuit of the plurality of measurement circuits to a corresponding second working electrode of the plurality of working electrodes, and electrically isolating the second measurement circuit from the corresponding second working electrode, and wherein measurements on each of the plurality of working electrodes are produced with respect to the counter electrode and/or the reference electrode.

17. The method of claim 16, wherein the operating mode comprises a 2-lead operating mode and a 3-lead operating mode, and wherein the multi-channel potentiostat circuit operates in the 2-lead operating mode when the first signal causes the stabilizing switch to close and the multi-channel potentiostat circuit operates in the 3-lead operating mode when the first signal causes the stabilizing switch to open.

18. The method of claim 17, wherein a default state of the stabilizing switch is closed to prevent a floating voltage.

19. The method of claim 17, wherein, when operating in the 3-lead operating mode, the second signal comprises a plurality of control signals, and the method further comprises sequentially closing each of the plurality of interference switches specified by the plurality of control signals to couple each of the plurality of measurement circuits to its corresponding working electrode of the plurality of working electrodes one-by-one.

20. The method of claim 17, wherein, when operating in the 3-lead operating mode, the second signal comprises a plurality of control signals, and wherein the method further comprises simultaneously closing two or more of the plurality of interference switches specified by the plurality of control signals to couple respective working electrodes of the plurality of working electrodes to their corresponding measurement circuits of the plurality of measurement circuits when the corresponding measurement circuits of the plurality of measurement circuits share a same voltage bias or a same voltammetry function.

* * * * *